(12) United States Patent
Hossack et al.

(10) Patent No.: US 7,988,633 B2
(45) Date of Patent: Aug. 2, 2011

(54) APPARATUS AND METHOD FOR USE OF RFID CATHETER INTELLIGENCE

(75) Inventors: Norman Hugh Hossack, Folsom, CA (US); Stephen C. Davies, Folsom, CA (US); Donald Mamayek, Mountain View, CA (US); Richard Scott Huennekens, San Diego, CA (US); Stephen Fry, El Dorado Hills, CA (US); Eric V. Mott, Rancho Cordova, CA (US); Peter Smith, Sacramento, CA (US); Scott Brownlie, Carmichael, CA (US); Jon D. Klingensmith, El Dorado Hills, CA (US); Richard Klosinski, Carmichael, CA (US); Ed Oliver, Folsom, CA (US); Masood Ahmed, Rocklin, CA (US); Gerald Lea Litzza, Sacramento, CA (US)

(73) Assignee: Volcano Corporation, Rancho Cordova, CA (US)

( * ) Notice: Subject to any disclaimer, the term of this patent is extended or adjusted under 35 U.S.C. 154(b) by 1688 days.

(21) Appl. No.: 11/250,159

(22) Filed: Oct. 12, 2005

(65) Prior Publication Data
US 2007/0083111 A1    Apr. 12, 2007

(51) Int. Cl.
*A61B 8/14*    (2006.01)
*A61B 8/00*    (2006.01)
(52) U.S. Cl. .................. 600/467; 600/437; 600/443
(58) Field of Classification Search .............. 600/443, 600/467, 437, 466
See application file for complete search history.

(56) References Cited

U.S. PATENT DOCUMENTS

| 4,868,476 | A | * | 9/1989 | Respaut ................. 318/632 |
| 5,487,386 | A | | 1/1996 | Wakabayashi |
| 5,544,660 | A | | 8/1996 | Crowley |
| 6,036,654 | A | | 3/2000 | Quinn |
| 6,248,083 | B1 | | 6/2001 | Smith |
| 6,266,551 | B1 | | 7/2001 | Osadchy |
| 6,270,460 | B1 | | 8/2001 | McMartan |
| 6,308,089 | B1 | | 10/2001 | Von der Ruhr |
| 6,387,092 | B1 | | 5/2002 | Burnside |

(Continued)

OTHER PUBLICATIONS

International Search Report for PCT/US06/39985 dated Aug. 16, 2007.

(Continued)

*Primary Examiner* — Long V Le
*Assistant Examiner* — Katherine L Fernandez
(74) *Attorney, Agent, or Firm* — Haynes and Boone, LLP (57) ABSTRACT

A method and system is provided for using backscattered data and known parameters to characterize vascular tissue. Specifically, methods and devices for identifying information about the imaging element used to gather the backscattered data are provided in order to permit an operation console having a plurality of Virtual Histology classification trees to select the appropriate VH classification tree for analyzing data gathered using that imaging element. In order to select the appropriate VH database for analyzing data from a specific imaging catheter, it is advantageous to know information regarding the function and performance of the catheter, such as the operating frequency of the catheter and whether it is a rotational or phased-array catheter. The present invention provides a device and method for storing this information on the imaging catheter and communicating the information to the operation console. In addition, information related to additional functions of the catheter may also be stored on the catheter and used to further optimize catheter performance and/or select the appropriate Virtual Histology classification tree for analyzing data from the catheter imaging element.

76 Claims, 6 Drawing Sheets

U.S. PATENT DOCUMENTS

| | | |
|---|---|---|
| 6,547,757 B1 * | 4/2003 | Kranz et al. ............... 604/95.04 |
| 6,578,579 B2 | 6/2003 | Burnside |
| 6,651,669 B1 | 11/2003 | Burnside |
| 6,659,940 B2 | 12/2003 | Adler |
| 6,733,495 B1 * | 5/2004 | Bek et al. ........................ 606/34 |
| 6,792,390 B1 | 9/2004 | Burnside |
| 6,847,490 B1 | 1/2005 | Nordstrom et al. |
| 6,861,954 B2 | 3/2005 | Levin |
| 6,985,870 B2 | 1/2006 | Martucci |
| 2003/0183683 A1 | 10/2003 | Stewart |
| 2004/0008123 A1 | 1/2004 | Carrender |
| 2004/0122326 A1 * | 6/2004 | Nair et al. .................... 600/467 |
| 2004/0172016 A1 | 9/2004 | Bek |
| 2004/0230116 A1 * | 11/2004 | Cowan et al. ................. 600/437 |
| 2004/0231772 A1 | 11/2004 | Leonard |
| 2005/0149358 A1 | 7/2005 | Sacco |
| 2005/0159802 A1 | 7/2005 | Furst |
| 2005/0196026 A1 | 9/2005 | Klingensmith et al. |
| 2005/0277873 A1 | 12/2005 | Stewart et al. |
| 2006/0065713 A1 | 3/2006 | Kingery |

OTHER PUBLICATIONS

Written Opinion for PCT/US06/39985 dated Aug. 16, 2007.

* cited by examiner

APPARATUS AND METHOD FOR USE OF RFID CATHETER INTELLIGENCE

FIELD OF THE INVENTION

The present invention relates to a system and method of using backscattered data and known parameters to identify and characterize vascular tissue, or more particularly, to devices and methods of use for identifying the operating frequency and type of catheter being used to acquire the backscattered data and for relaying specific information about the catheter to an attached operation console.

BACKGROUND OF THE INVENTION

Ultrasound imaging of the coronary vessels of a patient can provide physicians with valuable information regarding the identify the shape of a blood vessel, its density, its composition that can be useful in the diagnosis and/or treatment of a patient. For example, such information may show the extent of a stenosis in a patient, reveal progression of disease, determine the vulnerability of the atherosclerotic plaque for causing myocardial infarction, help determine whether procedures such as angioplasty, stenting or atherectomy are indicated, or whether more invasive procedures are warranted.

Currently, intravascular ultrasound (IVUS) devices use reflected ultrasound data to reproduce or image a blood vessel. In a typical ultrasound imaging system, an ultrasonic transducer is attached to the end of a catheter that is carefully maneuvered through a patient's body to a point of interest such as within a blood vessel. The transducer may be a single-element crystal or probe that is mechanically scanned or rotated back and forth to cover a sector over a selected angular range. Acoustic signals are then transmitted and echoes (or backscatter) from these acoustic signals are received. As the probe is swept through the sector, many acoustic lines are processed building up a sector-shaped image of the patient. These signals may then be processed using well known techniques and transformed into a gray scale image of the vasculature on a computer console in the catheter lab, i.e. an IVUS image.

More recently, the radio frequency signal from the backscatter data has been gathered and correlated with known histology data to permit further analysis and classification of the vasculature. This new Virtual Histology™ technology provides the ability to identify boundary features within the vasculature and plaque and to determine the composition of each patient's atherosclerotic plaques from the RF backscatter data. Currently, Virtual Histology mapping is accomplished by transforming the RF backscatter signal from an IVUS catheter into the frequency domain and then analyzing various power spectral characteristics to classify tissue in windows along each IVUS scan line according to a database, or classification tree, containing the specific spectrum RF signals for four plaque types, fibrous, fibro-fatty, dense calcium and necrotic core. Using this technology, Virtual Histology™ (VH) images generated from IVUS data can now show four plaque component types.

The VH databases, or classification trees, used to correlate the patient's IVUS data and identify tissue type are compiled by examining RF backscatter data from known histologic tissue types and correlating the spectral characteristics of the backscatter data with a specific tissue type. However, the VH classification trees must be computed using WUS catheters operating at a specific frequency since data obtained using catheters operating at other frequencies may result in different spectral characteristics for a given tissue. Thus, separate VH classification trees must be generated for each catheter operating frequency and the patient data obtained from a catheter operating at a specific frequency must be correlated with the classification tree for that operating frequency in order to achieve an accurate mapping of the patients vasculature and classification of the vascular tissue and plaque type. Currently IVUS catheters operating at 20 MHz, 30 MHz and 40 MHz are commercially available. In addition, there are several types of ultrasonic transducers capable of gathering and transmitting the frequency spectrum of RF signal backscattered from vascular tissue needed to characterize the vascular tissue. For example, phased array IVUS catheters or rotational IVUS catheters, such as those disclosed in such as disclosed in U.S. Pat. No. 5,368,037, issued to Eberle and U.S. Pat. No. 5,000,185, issued to Yock, both fully incorporated herein by reference, may be used to gather RF data. However, once again, different VH classification trees must be generated for data obtained from phased array vs. rotational IVUS catheters.

Early imaging catheters typically relied on manual recognition of a catheter type. For example, catheters were color coded according to type then the operator had to manually input this information into an operation console. Other early alternatives included measuring the catheter resistance to determine the operating frequency or storing catheter information in an EPROM located in the catheter connector. However, with the use of multiple VH classification databases to analyze data from catheters with different operating frequencies or modes of use, the identification and communication of catheter operating information from the catheter to the operation console is critical.

Thus, new devices and methods are needs for identifying information regarding the IVUS catheter being used, for example the catheter type, operational frequency, individual performance characteristics and/or calibration coefficients, etc, and relaying that information to an attached operator's console to assist in selection of the appropriate VH classification tree for analyzing the RF data obtained from the IVUS catheter.

SUMMARY OF THE INVENTION

The present invention provides a method and devices for communication between an imaging catheter and an operation console to select the appropriate VH classification database. In order to select the appropriate VH database for analyzing data from a specific imaging catheter, it is advantageous to know information regarding the operating frequency of the catheter and whether it is a rotational or phased-array catheter. However, additional information regarding specific catheter performance characteristics such as the unity gain value, the boot mode, the catheter sensitivity may also be stored on the catheter and used to further optimize, catheter performance and/or select the appropriate VH tree for analyzing data from the catheter imaging element.

In an embodiment according to the present invention, a Radio Frequency Identification (RFID) chip, such as a Maxwell ME1 or ME2 RFID chip, mounted on a connector on the proximal end of the catheter, is used to store information about the catheter. RFID technology is a wireless technology for data transfer previously used in applications, such as electronic toll collection, railway car identification and tracking, that offers automatic identification functionality as well as the ability to easily and securely store, transfer and update information. RFID provides certain advantages over prior catheter identification systems. For example, the RFID chip may have a memory capacity of several kilobytes or more, which is substantially greater than the maximum amount of data that may be acquired from the prior methods of catheter identification. The information initially stored on the RFID tag may include identifying information about the catheter such as make, model and serial number, operational characteristics of the catheter, such as operating frequency, type of imaging element, calibration coefficients, sensitivity, and boot mode, and use limitations, such as expiration date, geographic region of use, permissible number of uses or permissible time of use. In addition, the short transmission distance of the RFID chip may avoid interfering with other electronic equipment in the cath lab.

The RFID technology may also include an antenna capable of reading and writing additional information to the chip. In such an embodiment, the information regarding the catheter may be updated, for example, as the catheter is used and the performance characteristics and/or calibration coefficients for a given operating frequency or catheter model change.

The catheter interface device includes an RFID scanner mounted in proximity to the connector on the interface device for the catheter. In an embodiment according to the present invention, the catheter interface device may be a pull back device used to operate an IVUS catheter. Here, the RFID scanner is mounted so that when the catheter connecter and the pullback device connector are joined the RFID scanner is located within the given transmitting distance for the RFID chip on the catheter, for example between about 0-10 mm. When the catheter is connected to the pullback device, the catheter connector triggers a trip switch located in the interface device connector and activates the RFID scanner. The RFID scanner may then read the information on the catheter RFID chip to determine the identity of the catheter. The interface device may then relay the catheter identification information to the operation console. The interface device may be connected to the operation console via any suitable communication protocol, for example via a USB or serial connection. Once the interface device relays the information to the operation console, the interface device may turn off the RFID scanner.

The information relayed to the operation console may include one or more of the catheter serial number, catheter name, catheter model number, calibration coefficients, time gain control, post amp gain, date of first use, date of last use, number of times used, number of permissible uses, geographic location of permissible use, boot mode, pulse width, or expiration date of the catheter to the operation console. The operation console may then use this information to determine which of the multiple VH classification databases stored on the operation console should be used to analyze the data captured using this catheter and imaging element. For example, the operation console may choose the VH classification tree based on the operating frequency of the attached catheter. Alternatively, the catheter RFID chip may contain additional information regarding sensitivity of the catheter, in which case, the operation console may choose a VH classification tree based on operating frequency of the catheter and a high, medium or low sensitivity rating. In an alternative embodiment, once the operation console has selected a VH classification tree using information stored on the catheter RFID chip, the operation console may use additional information relayed from the catheter RFID chip, such as boot mode, time gain control, post amp gain or other calibration coefficients to further optimize the catheter performance and data analysis.

In addition, the operation console may use the information from the catheter RFID chip to determine whether or not to permit catheter operation. In an alternative embodiment, the catheter RFID chip may further store a security code for the catheter. This security code may be read by the RFID reader on the interface device and if the catheter security code is not authorized for use with the connected catheter interface device, the system will not permit the catheter use. In an alternative embodiment, the catheter RFID chip may further store an expiration date. This expiration date may be read by the RFID reader on the interface device and if the expiration date had passed, the interface device may prohibit catheter use. In another alternative embodiment, the RFID chip may be programmed to permit a given number of uses or hours of use. Here, the RFID chip may be updated after each use to store the total number of uses or total hours of use. When the catheter is connected to an interface device, the interface device may read and compare the values for the permissible hours of use/times used with the total hours of use/times used. Once the total number of uses or total hours of use surpasses the pre-programmed limit, the interface device may prohibit catheter use.

In an alternative embodiment, the RFID scanner located on the interface device may further include RFID read and write capabilities. Here, the operation console may instruct the interface device to turn on the RFID scanner at the end of a catheter use to download information regarding the catheter use to the RFID chip. For example, the operation console may download patient identification, hospital information and operating physician information to the RFID chip. In addition, it is envisioned that at the completion of a clinical procedure, the Virtual Histology images themselves may be downloaded and stored on the catheter RFID chip along with the patient information and used as a medical record of the procedure. The RFID chip may also be designed so that it can be removed in order to provide an easily transportable record of the complete procedure that may used with another with another RFID reader to transfer the information to a different storage medium or analysis device.

In an alternative embodiment, the RFID scanner may also be used to update the operational and performance characteristics and use information of the catheter for future catheter use. When more than a single use is permissible, the catheter may have a shield, for example lead, positioned over the RFID chip to protect the RFID chip during a severe sterilization process, such as radiation. In addition, if upon removal it is desired that the RFID chip be sterile, for example for transfer at bedside, the RFID chip may be presterilized using gas and sealed hermetically prior to positioning the shield.

A more complete understanding of the method and system for vascular tissue characterization will be afforded to those skilled in the art, as well as a realization of additional advantages and objects thereof, by a consideration of the following detailed description of the preferred embodiment. Reference will be made to the appended sheets of drawings, which will first be described briefly.

DETAILED DESCRIPTION OF THE INVENTION

Figure 1:
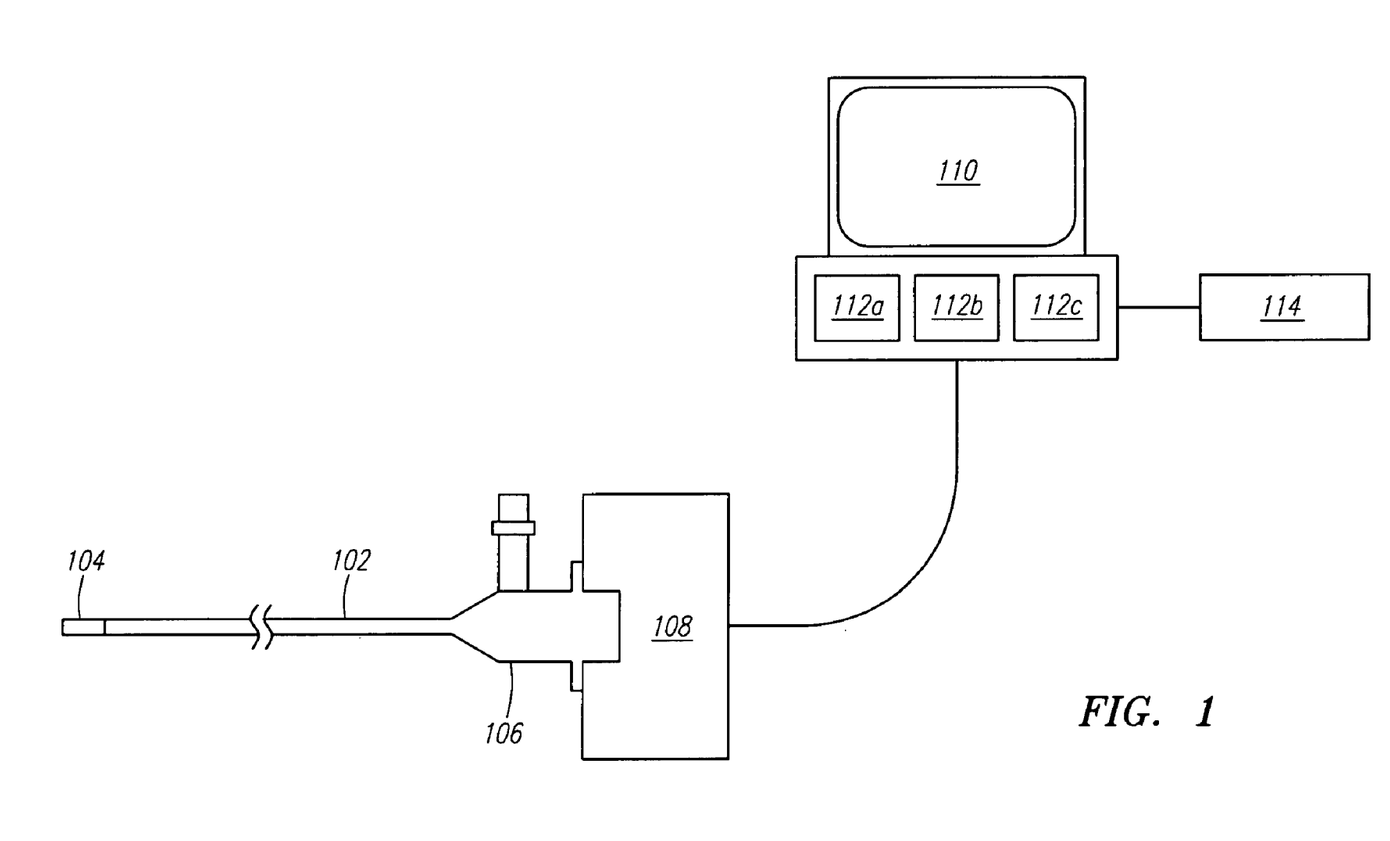
FIG. 1 is a block diagram depicting a system for vascular tissue characterization according to the present invention.

FIG. 1 is a block diagram showing an embodiment of a system for characterizing vascular tissue data. The system generally comprises a catheter 102, having an imaging element 104 operably connected at the distal end, connected to an interface device 108 which is then connected to an operation console 110. When the catheter 102 is connected to the interface device 108, the interface device 108 is triggered and begins reading catheter information stored on a memory device, for example an EPROM, an RFID chip or other suitable memory device, located on the catheter 102. The catheter 102 relays information about the imaging element 104 to the interface device 108. At a minimum, the catheter may communicate the type of imaging element, for example phased array ultrasonic transducers or rotational ultrasonic transducers, and operating frequency of the imaging element. However, the catheter may also relay additional information regarding specific catheter identification and/or performance characteristics, for example catheter serial number, name, make or model, calibration coefficients, imaging element sensitivity, time gain control, post amp gain, date of first use, date of last use, number of times used, number of permissible uses, geographic location of permissible use, boot mode, pulse width, or expiration date of the catheter to the operation console.

The interface device 108 then relays the catheter information to the operation console 110. The interface device 108 may be connected to the operation console 110 via any suitable communication protocol known in the art, for example USB or Serial. In an alternative embodiment, the catheter may be directly connected to the operation console, In another alternative embodiment, the information transfer may be via a wireless communication protocol. The operation console 110 contains a plurality Virtual Histology classification trees 112a-c each developed using known method of comparing histology data and IVUS data gathered by different types of catheters operating at different frequencies.

Currently, Virtual Histology classification trees are developed by collecting and correlating RF backscatter signal from an IVUS catheter with known histologic tissue types as disclosed in U.S. patent application Ser. No. 10/647971, fully incorporated herein by reference. The RF data is transformed in to the frequency domain and the various power spectral characteristics of the backscattered signal are correlated with characterization data to determine signature parameters for each tissue type. However, these spectral characteristics of the tissue types vary for catheters operating at different frequencies and thus separate classification trees must be used. Accordingly, specific information about the catheter used for a clinical procedure is needed to select the appropriate classification tree for analyzing that data.

The information from the catheter, at a minimum-the operating frequency of the connected catheter 102, is used by the operation console 110 to select the appropriate VH classification tree 112a-c for analyzing incoming IVUS data. In addition, information regarding specific catheter performance characteristics such as the unity gain value, the boot mode, the catheter sensitivity may also be stored on the catheter and used to further select the appropriate VH tree for analyzing data from the catheter imaging element. For example, it is envisioned that the operation console 110 could store VH classification trees for low, medium and high sensitivity catheters in each operating frequency. Then, based on information from the catheter regarding the operating frequency and sensitivity of the catheter, the operation console further tailor the selection of the appropriate VH classification tree. In an alternative embodiment, the VH classification tree for the specific catheter may be stored on the catheter. Here, when the catheter is placed in communication with the interface device, the catheter will relay the specific classification tree to use for analyzing the data it collects to the operation console and the operation console will simply download the classification tree from the catheter.

Once the clinical procedure is complete, the operation console 110 may download the VH image and data to the catheter for storage within the catheter memory device and either the entire catheter, the catheter connector containing the RFID chip or the removable RFID chip may then be used as a portable medical record. Alternatively, if the catheter is approved for reuse, the operation console may down load specific information regarding the time and duration of use of the clinical procedure to the catheter. This information may be stored and tracked on the catheter monitor and limit the number of uses or hours of use to a predetermined amount also stored on the catheter.

Figure 2:
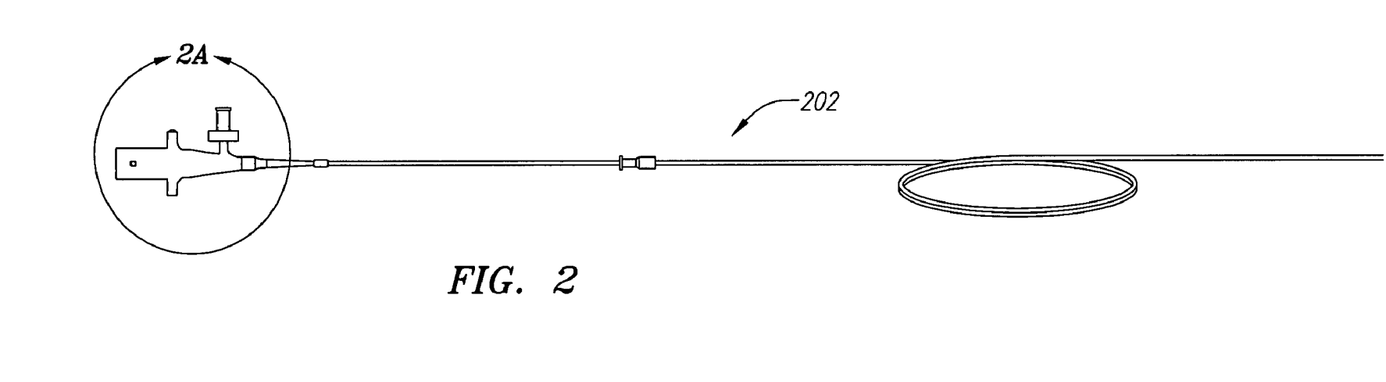
FIG. 2 illustrates an embodiment of a catheter for use according to the present invention
Figure 2A:
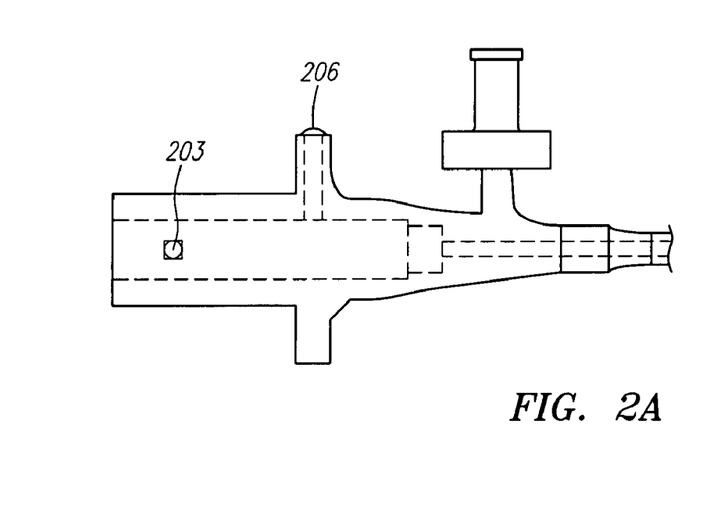
FIG. 2A illustrates an embodiment of a catheter connector containing an RFID chip for use according to the present invention.
Figure 2B:
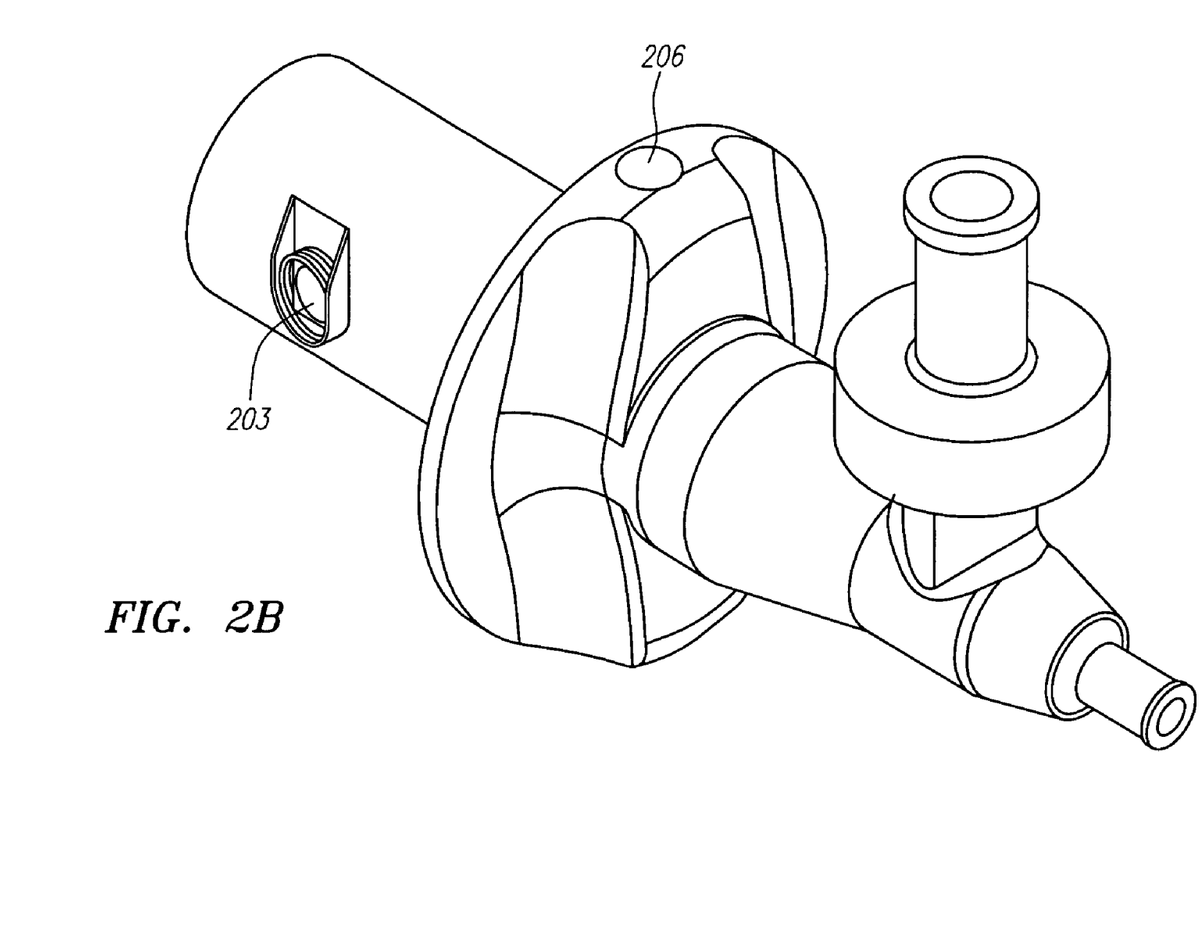
FIG. 2B illustrates an embodiment of a catheter connector containing an RFID chip for use according to the present invention.
Figure 3:
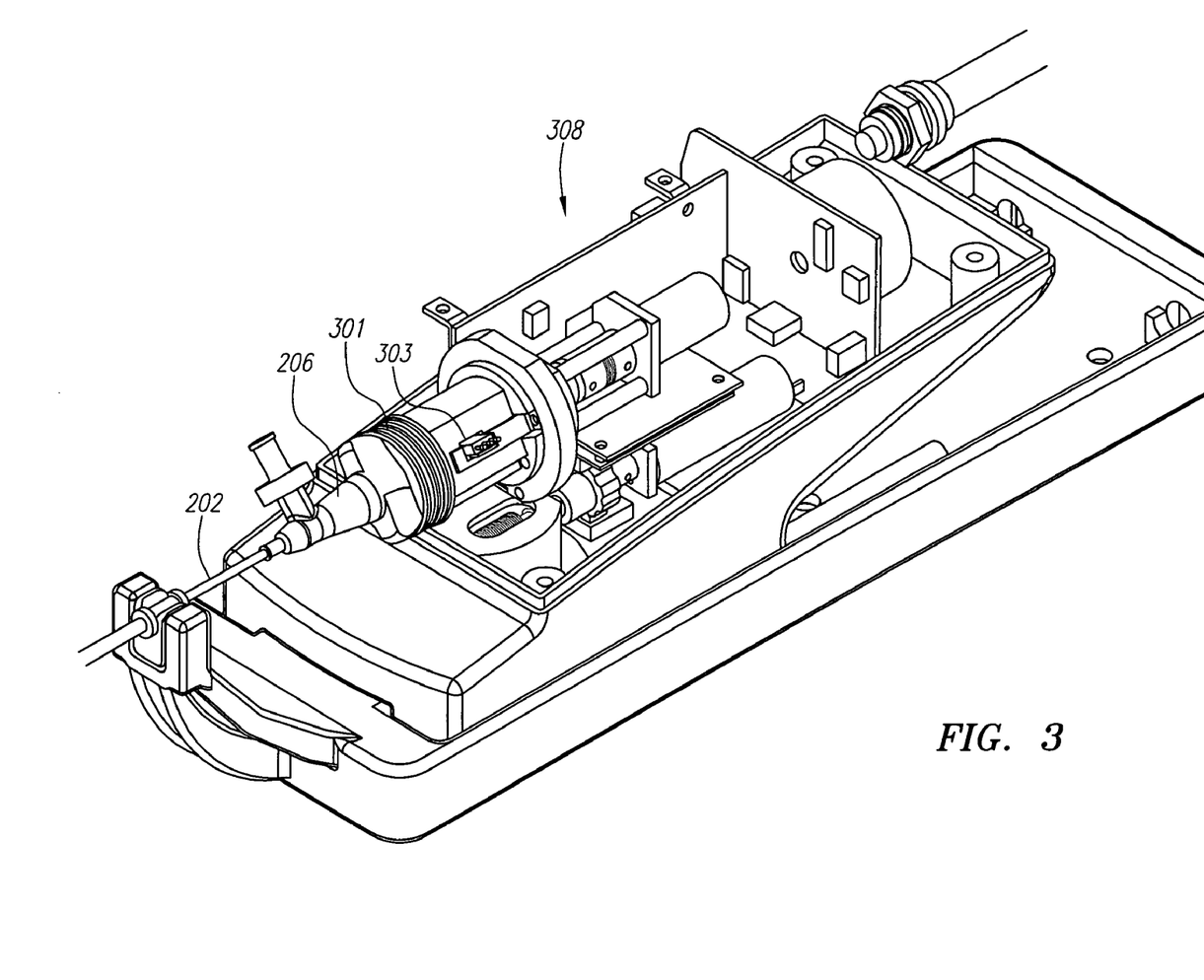
FIG. 3 illustrates an embodiment of a pull back device for use according to the present invention.
Figure 3A:
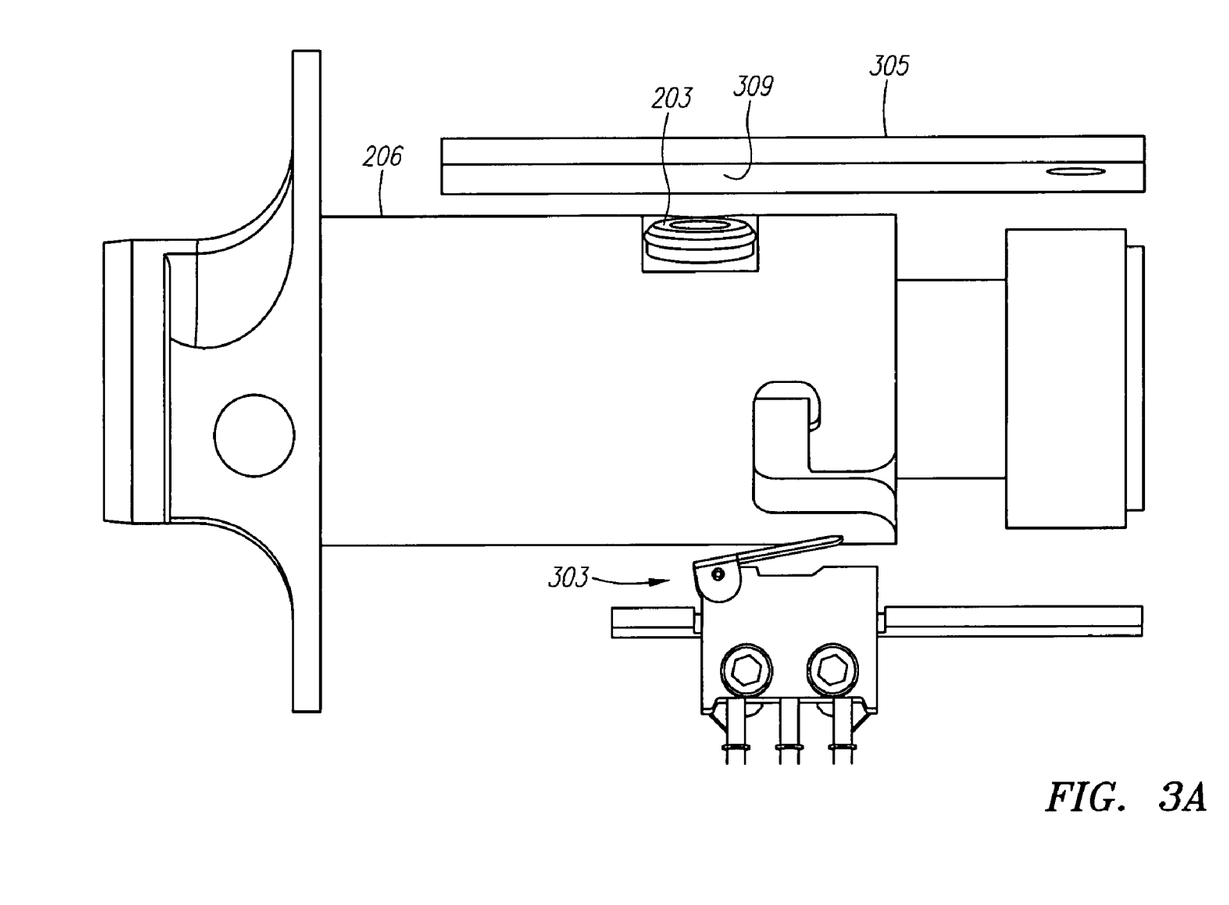
FIG. 3a illustrates an embodiment of a pull back device for use according to the present invention.

In one embodiment according to the present invention, as shown in FIG. 2-3, the catheter 202 may have an RFID chip 203, such as Maxwell ME1 or ME2 RFID chip, mounted on the connector 206 on the proximal end of the catheter 202 for storing information and communicating with the interface device 308. In an alternative embodiment, the catheter may have a second RFID chip (not shown) mounted 180 degrees from the first RFID chip 203 of the connector 206 so catheter can be connected to interface device at more than one circumferential orientation. The RFID chip 203 may have a memory of 128 bytes, alternatively 1K byte, alternatively 2K bytes alternatively 4K bytes to store catheter specific information, including for example catheter serial number, name, make or model, calibration coefficients, imaging element sensitivity, time gain control, post amp gain, number of permissible uses, geographic location of permissible use, boot mode, pulse width, or expiration date of the catheter. Here, when the catheter connector 206 is inserted into the connector 301 on the interface device, the catheter connector 206 engages a trip switch 303 which activates the RFID circuit board 305 to start the RFID scanner 309 looking for the catheter RFID chip 203. The RFID scanner 309 is located near the connection point of two connectors. Thus, when the connectors 206 and 301 are properly joined, the RFID scanner will be with in transmission distance, about 0-10 mm, alternatively about 0-3 mm, from the RFID chip 203 located on the catheter connector 206. The RFID scanner 309 reads the information stored on the catheter RFID chip 203 and relays this information to the RFID circuit board 305. The RFID circuit board 305 may optionally include a microprocessor and instructions for processing and acting on some of the data received from the catheter RFID chip 203 . For example, the catheter RFID chip 203 may transmit a security code which must be matched by a corresponding security code on the interface device in order to authorize catheter use. In addition, the RFID scanner 309 may have read and write capability, in which case the RFID circuit board 305 may further include instructions for writing additional information to the catheter RFID chip 203. This information could be useful for tracking the catheter and for ensuring security and sterility of the catheter. For example, the RFID circuit board 305 may receive information from the operation console regarding the patient identification, hospital, operating physician, which could be downloaded and stored on the RFID chip 203. In addition, it is envisioned that at the completion of a clinical procedure, the Virtual Histology images themselves, along with the corresponding patient information may be downloaded and stored on the catheter RFID chip which may then be removed from the catheter and used as a medical record of the procedure. Alternatively, information regarding the time of use, duration of the procedure and interface device used could be downloaded to the RFID chip to monitor and manage sterility of the catheter. For example, once a catheter is connected to a particular interface device, then the catheter will only operate with that interface device for a limited time period, such as 8 hours, or 12 hours or the typical length of a given procedure. The operation console can monitor the duration of use of the catheter and download this information to the catheter RFID chip so that if the catheter is plugged into another interface device, use will not be permitted. If the catheter fails during use, the operation console may also download a failure code as well as complete information regarding the circumstances of the failure to the RFID chip.

Figure 4:
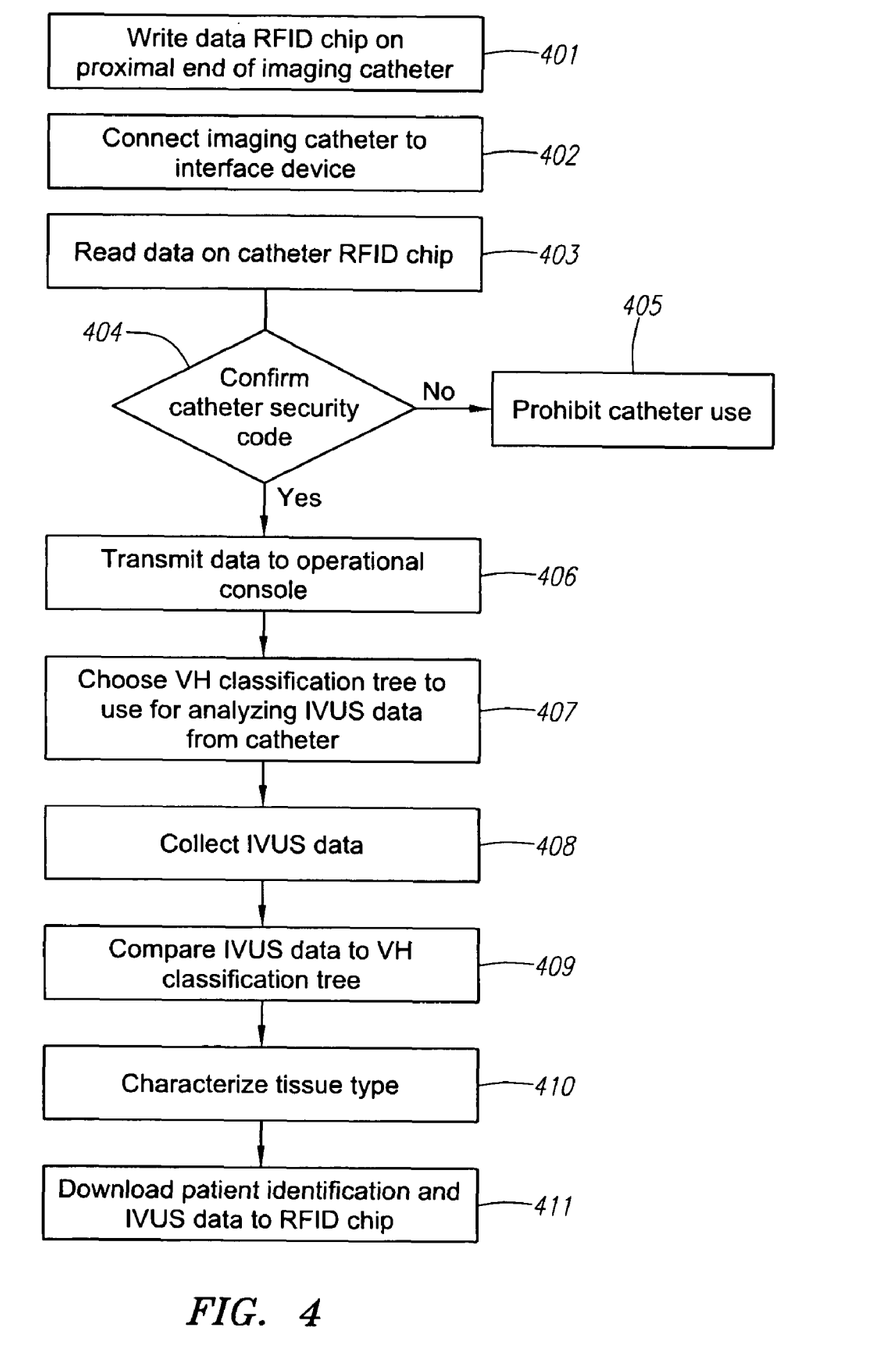
FIG. 4 is a flow chart illustrating exemplary steps for identifying an imaging catheter and selecting the appropriate classification tree for analyzing data from the attached catheter

FIG. 4 shows exemplary steps of a method for characterizing vascular tissue data using RFID chip mounted on the proximal end of the catheter for communicating catheter information to the operation console to select the appropriate classification tree. Those skilled in the art will realize that the same methods may be implemented by a system for characterizing vascular tissue data using different methods of storing, transferring and receiving data between the catheter and operation console. At step 401, data regarding the identification and operating characteristics of the catheter is stored on an RFID chip located on the proximal end of the catheter. This may include one or more of the catheter serial number, catheter name, catheter model number, calibration coefficients, time gain control, post amp gain, date of first use, date of last use, number of times used, number of permissible uses, geographic location of permissible use, boot mode, pulse width, or expiration date of the catheter to the operation console.

At step 402, the catheter is connected to an interface device. For example, , the interface device may be a pullback device, such as the Volcano™ Revolution™ PIM, or the Volcano™ R100, for operation of a rotational or phased array IVUS catheter. The connection between the catheter and the interface device activates the interface device, and at step 403, an RFID scanner on the interface device reads the catheter identification and operating data stored on the catheter RFID chip. The interface device may further comprise a microprocessor for initially processing some of the data from the RFID chip, or the interface device may simply relay the information to the operation console for processing. For example, at step 404, the interface device may read a security code or expiration date stored on the RFID chip and if the security code is not authorized or the expiration date has passed, at step 405 the interface device may prohibit operation of the catheter.

At step 406, the interface device transfers the information from the catheter RFID chip to the attached operation console using a standard communication protocol, such as USB or serial. At step 407, the operation console uses this data to select one of multiple VH classification trees for analyzing data received from that catheter. For example, the operation console may use data regarding the catheter model number to determine whether the catheter is a phased array or rotational IVUS catheter. The operation console may then use the data regarding the catheter operating frequency to select the classification tree corresponding to that catheter type with that operating frequency.

At step 408, the interface device operates the catheter to collect IVUS data from the imaging element located in the patient's vasculature. The interface device may use information regarding the catheter performance characteristics that was stored on the RFID chip, for example the catheter boot mode, to operate the catheter. The IVUS data is transmitted to the operation console where it is processed and analyzed. Once again, the operation console may use information received from the catheter RFID chip to process and optimize the IVUS data, e.g. RF backscatter data. For example, the time gain control, post amp gain and pulse width data regarding the catheter signal stored on the RFID chip may be used to process IVUS data.

At step 409, the spectral parameters of the IVUS data are identified and compared to parameters stored in the VH classification tree for each of the known tissue types, including fibrous tissue, fibro-fatty, necrotic core, dense calcium, thrombus, organized thrombus, blood, highly vascular tissue and not highly vascular tissue. In addition, non-tissue material, such as stent material, can also be identified. In areas where the signal is too low to characterize tissue with a high level of confidence, the image can be blacked out to avoid misinterpretation of the image. The same process can also be used in other applications to identify myocardium or cancer cells. At step 410, if a match (either exactly or substantially) is found, the region related with that parameter is correlated to the tissue type stored in the VH classification tree.

At step 411, once the clinical procedure is complete, the information regarding the characterization of the tissue is downloaded to the RFID chip via the interface device. In addition, the operation console may transmit additional information regarding the procedure, including for example patient identification, operating physician, hospital information, time and duration of procedure, etc. In this way, the RFID chip could be used as a complete medical record of the procedure.

Having thus described a preferred embodiment of a method and system for characterizing vascular tissue, it should be apparent to those skilled in the art that certain advantages of the within system have been achieved. It should also be appreciated that various modifications, adaptations, and alternative embodiments thereof may be made within the scope and spirit of the present invention. For example, a system using an RFID device for communication between the catheter and operation console has been illustrated, but it should be apparent that the inventive concepts described above would be equally applicable for any number communication methods between the catheter and operation console. In addition, the invention is not limited to a particular type of IVUS catheter, and may used in the characterization of IVUS data from rotational as well as phased array IVUS catheters. The invention is defined by the following claims.

We claim:

1. A method of identifying a catheter comprising:
attaching a catheter to a catheter interface device wherein the catheter further comprises an RFID chip located on a proximal end of the catheter and wherein the catheter interface device further comprises an RFID scanner;
reading information related to a function of the catheter stored on the catheter RFID chip with the RFID scanner;
identifying at least one operating characteristic related to the function of the catheter based on the information related to the function of the catheter read from the RFID chip, the at least one operating characteristic including an operating frequency of an imaging transducer associated with the catheter; and using the at least one operating characteristic related to the function of the catheter as a parameter in characterizing a tissue imaged by the imaging transducer.

2. The method of claim 1, wherein the information related to the function of the catheter is selected from a group consisting of catheter serial number, catheter name, catheter make, catheter model, calibration coefficients, time gain control, post amp gain, date of first use, date of last use, number of uses, hours of use, boot mode, pulse width, expiration date, number of permissible uses, hours of permissible use, geographic region of permissible use, failure codes, and patient information.

3. The method of claim 1, wherein the catheter interface device is operably connected to an operation console, further comprising the step of relaying the at least one characteristic related to the function of the catheter to the operation console.

4. The method of claim 3, further comprising the step of relaying additional information related to the function of the catheter to the operation console.

5. The method of claim 3, further comprising the step of updating information related to the function of the catheter on the RFID chip.

6. The method of claim 5, wherein the updating step further comprises the step of downloading updated information related to the function of the catheter from the operation console.

7. The method of claim 1, further comprising the steps of:
inserting the catheter into a patient's vasculature;
gathering data regarding the patient's vasculature while the catheter is operating;
monitoring catheter operation; and
downloading information related to the catheter operation to the RFID chip.

8. The method of claim 7, further comprising the step of downloading the data regarding a patient's vasculature to the catheter RFID chip.

9. The method of claim 7, further comprising the step of downloading patient identification data to the catheter RFID chip.

10. The method of claim 7, wherein monitoring step further comprises monitoring the actual time the catheter was is use and wherein the downloading information related to the catheter operation step further comprises downloading the actual time the catheter was in use to the catheter RFID chip.

11. The method of claim 10, further comprising the steps of:
storing the time of permissible use on the catheter RFID chip;
comparing the actual time of use to the time of permissible use; and
prohibiting subsequent use of the catheter once the time of use is equivalent to the permissible time of use.

12. The method of claim 7, further comprising the steps of monitoring catheter operational failure; and
downloading data regarding the catheter failure to the catheter RFID chip.

13. The method of claim 12, further comprising the step of prohibiting subsequent use of the catheter based on presence of failure data.

14. The method of claim 7, further comprising the step of storing information related to the catheter operation on the catheter RFID chip.

15. The method of claim 14, wherein information related to the catheter operation stored on the catheter RFID chip is selected from a group consisting of: calibration coefficients, time gain control, post amp gain, date of first use, date of last use, number of uses, hours of use, boot mode, pulse width, expiration date, number of permissible uses, hours of permissible use, geographic region of permissible use, failure codes, or patient information.

16. The method of claim 14, further comprising the step of using the stored information related to the catheter operation to make a decision regarding subsequent catheter use.

17. A method of identifying an imaging catheter comprising:
attaching an imaging catheter to a catheter interface device wherein the imaging catheter further comprises an imaging element located on the distal end of the catheter and an RFID chip, storing information related to the function of the catheter, located on the proximal end of the catheter and wherein the catheter interface device further comprises an RFID scanner and is operably connected to an operation console;
reading information related to the function of the catheter from the catheter RFID chip with the RFID scanner;
identifying at least one characteristic relating to the function of the catheter based on the information related to the function of the catheter read from the RFID chip; and
using the at least one characteristic relating to the function of the catheter as a parameter in characterizing a tissue imaged by the imaging element.

18. The method of claim 17, wherein the information related to the function of the catheter is selected from a group consisting of catheter serial number, catheter name, make, or model, calibration coefficients, time gain control, post amp gain, date of first use, date of last use, number of uses, hours of use, boot mode, pulse width, expiration date, number of permissible uses, hours of permissible use, geographic region of permissible use, failure codes, or patient information.

19. The method of claim 17, wherein the at least one characteristic relating to the function of the catheter is further related to an operating frequency of the catheter.

20. The method of claim 19, further comprising the step of relaying additional information related to the function of the catheter to the operation console.

21. The method of claim 20, further comprising the step of using the additional information related to the function of the catheter to make a decision regarding catheter use.

22. The method of claim 20, wherein the additional information related to the function of the catheter is utilized in selecting the Virtual Histology classification tree for analyzing RF image data.

23. A method of identifying an imaging catheter comprising:
attaching an imaging catheter to a catheter interface device wherein the imaging catheter further comprises an imaging element located on the distal end of the catheter and an RFID chip, storing information related to the function of the catheter, located on the proximal end of the catheter and wherein the catheter interface device further comprises an RFID scanner and is operably connected to an operation console;
reading information related to the function of the catheter from the catheter RFID chip;
identifying at least one characteristic relating to the function of the catheter, wherein the at least one characteristic relating to the function of the catheter is further related to the type or operating frequency of the catheter;
relaying the at least one characteristic relating to the function of the catheter from the RFID scanner to an operation console;

relaying additional information related to the function of the catheter to the operation console;

using the additional information related to the function of the catheter to select a Virtual Histology classification tree for analyzing RF image data;

inserting the catheter into a patient's vasculature;

gathering RF backscattered data from vascular tissue while the catheter is operating; and using the Virtual Histology classification tree and the backscattered RF data to generate a Virtual Histology image of the vascular tissue.

24. The method of claim 23, further comprising the step of downloading and storing patient identification information on the catheter RFID chip.

25. The method of claim 23, further comprising the steps of:

monitoring catheter operation; and downloading and storing information related to the catheter operation to the catheter RFID chip.

26. The method of claim 25, further comprising the step of using information related to the catheter operation to make a decision regarding subsequent catheter use.

27. The method of claim 23, further comprising the step of downloading and storing the Virtual Histology image on the catheter RFID chip.

28. The method of claim 27, further comprising the step of encrypting the data stored on the RFID chip.

29. A system for identifying catheter performance characteristics comprising:

a catheter having distal and proximal ends and a lumen extending therebetween, wherein a first connector is located on the proximal end and wherein the catheter further comprises an imaging transducer;

an RFID chip mounted on the proximal end of the catheter and configured to store information related to at least one operating characteristic related to a function of the catheter;

a catheter interface device configured to control movement of the catheter, the catheter interface device having a second connector adapted to be coupled to the first connector, wherein the catheter interface device further comprises an RFID scanner located in proximity to the second connector such that the RFID scanner is able to read the RFID chip mounted on the catheter when the first connector is coupled to the second connector; and a processor configured to characterize a tissue imaged by the imaging transducer based on the at least one operating characteristic related to the function of the catheter.

30. The system of claim 29, wherein the RFID chip is adapted to store information about the catheter.

31. The system of claim 30, wherein the information is selected from a group consisting of catheter serial number, catheter name, catheter model number, calibration coefficients, time gain control, post amp gain, date of first use, date of last use, number of times used, number of permissible uses, geographic location of permissible use, boot mode, pulse width, expiration date of the catheter.

32. The system of claim 31, wherein the RFID scanner is an RFID reader.

33. The system of claim 32, wherein the RFID scanner is a read/write scanner.

34. The system of claim 33, wherein the catheter interface device further comprises a microprocessor for controlling reading and writing to the RFID chip.

35. The system of claim 31, wherein the catheter interface device is operably connected to an operation console.

36. The system of claim 35, wherein the operation console is connected to the catheter interface device via a serial port.

37. The system of claim 35, wherein the operation console is connected to the catheter interface device via a USB port.

38. The system of claim 35, wherein the operation console further comprises the processor, the processor further configured for controlling catheter operation based on information stored on the RFID chip.

39. The system of claim 29, wherein the RFID chip has a transmission distance of about 0-5 mm.

40. The system of claim 29, wherein the RFID chip has a transmission distance of about 5-15 mm.

41. The system of claim 29, wherein the RFID chip has a transmission distance of about 15-25 mm.

42. The system of claim 29, wherein the RFID chip has a memory of 128 bytes or less.

43. The system of claim 29, wherein the RFID chip has a memory of at least 1 K byte.

44. The system of claim 29, wherein the RFID chip has a memory of at least 2 K bytes.

45. The system of claim 29, wherein the RFID chip has a memory of at least 4 K bytes.

46. A system for characterizing vascular tissue data comprising:

a catheter having distal and proximal ends and a lumen extending therebetween, wherein a first connector is located on the proximal end;

an ultrasonic imaging element operably coupled to the distal end of the catheter;

an RFID chip mounted on the proximal end of the catheter and configured to store information related to a function of the catheter;

a catheter interface device having a second connector configured to interface with the first connector, the catheter interface device configured to control movement of the catheter when the first connector is coupled to the second connector, wherein the catheter interface device further comprises a RFID scanner located in proximity to the second connector such that the RFID scanner is able to read the RFID chip mounted on the proximal end of the catheter when the first connector is coupled to the second connector;

an operation console operably connected to the catheter interface device comprising a database configured to store a plurality of Virtual Histology classification trees for characterizing vascular tissue, wherein at least one of the Virtual Histology classification trees is stored on the RFID chip; and wherein the operation console further comprises a processor configured to select a Virtual Histology classification tree from the plurality of Virtual Histology classification trees based on the information related to the function of the catheter.

47. The system of claim 46, wherein the RFID chip is programmed to store information about the catheter.

48. The system of claim 47, wherein the information is selected from a group consisting of catheter serial number, catheter name, catheter model number, calibration coefficients, time gain control, post amp gain, date of first use, date of last use, number of times used, number of permissible uses, geographic location of permissible use, boot mode, pulse width, expiration date of the catheter.

49. The system of claim 48, wherein the RFID scanner is an RFID reader.

50. The system of claim 49 wherein the RFID scanner is a read/write scanner.

51. The system of claim 50, wherein the catheter interface device further comprises a microprocessor for controlling reading and writing information to the RFID chip.

52. The system of claim 51, wherein the microprocessor further includes instructions for controlling catheter operation based on information received from the RFID chip.

53. The system of claim 48, wherein the operation console is connected to the catheter interface device via a USB port.

54. The system of claim 48, wherein the operation console is connected to the catheter interface device via a serial port.

55. The system of claim 48, wherein the processor is further configured for controlling catheter operation based on information stored on the RFID chip.

56. The system of claim 46, wherein the RFID chip has a transmission distance of about 0-5 mm.

57. The system of claim 46, wherein the RFID chip has a transmission distance of about 5-15 mm.

58. The system of claim 46, wherein the RFID chip has a transmission distance of about 15-25 mm.

59. The system of claim 46, wherein the RFID chip has a memory of 128 bytes or less.

60. The system of claim 46, wherein the RFID chip has a memory of at least 1 K byte.

61. The system of claim 46, wherein the RFID chip has a memory of at least 2 K bytes.

62. The system of claim 46, wherein the RFID chip has a memory of at least 4 K bytes.

63. The system of claim 46, wherein the RFID chip further includes a unique security code.

64. The system of claim 46, wherein the RFID chip is encrypted.

65. The system of claim 46, wherein the RFID chip further includes information regarding other imaging modalities contained on the catheter.

66. A system for characterizing vascular tissue data comprising:
 a catheter further comprising:
  an ultrasonic imaging element operable within a distal region of the catheter; and
  a communication device for transmitting information about the catheter;
 an operation console further comprising a memory arranged to store a plurality of Virtual Histology classification trees; and
 a processor configured to receive information from the catheter and select a Virtual Histology classification tree from the plurality of Virtual Histology classification trees based on the information received from the catheter;
 wherein the plurality of classification trees further comprises at least a first classification tree which represents data derived from an IVUS catheter having a first operating frequency and at least a second classification tree which represents data derived from an IVUS catheter having a different operating frequency from the first operating frequency.

67. The system of claim 66, wherein the catheter further comprises a memory arranged to store information about the catheter.

68. The system of claim 67, wherein the information about the catheter is selected from a group consisting of catheter serial number, catheter name, make, or model, calibration coefficients, time gain control, post amp gain, date of first use, date of last use, number of uses, hours of use, boot mode, pulse width, expiration date, number of permissible uses, hours of permissible use, geographic region of permissible use, failure codes, or patient information.

69. The system of claim 66, further comprising a catheter interface device wherein the proximal end the catheter is operably connected to the catheter interface device and the operation console is operably connected to the catheter interface device further comprising:
 a first communication connection configured for receiving and transmitting information from the catheter; and
 a second communication connection configured for receiving and transmitting information from the operation console.

70. The system of claim 69, wherein the catheter interface device further comprises a processor configured to transfer information from the operation console to the catheter.

71. The system of claim 66, wherein the catheter further comprises a memory arranged to store information regarding the catheter operating frequency and wherein the processor is configured to select the classification tree based on the catheter operating frequency.

72. A system for characterizing vascular tissue data comprising:
 a catheter further comprising:
  an ultrasonic imaging element operable within a distal region of the catheter; and
  a communication device for transmitting information about the catheter;
 an operation console further comprising a memory arranged to store a plurality of Virtual Histology classification trees; and
 a processor configured to receive information from the catheter and select a Virtual Histology classification tree from the plurality of Virtual Histology classification trees based on the information received from the catheter,
 wherein the plurality of classification trees further comprises at least a first classification tree which represents data derived from a rotational IVUS catheter and at least a second classification tree which represents data derived from a phased array IVUS catheter.

73. The system of claim 72, wherein the catheter further comprises a memory arranged to store information about the catheter.

74. The system of claim 73, wherein the information about the catheter is selected from a group consisting of catheter serial number, catheter name, make, or model, calibration coefficients, time gain control, post amp gain, date of first use, date of last use, number of uses, hours of use, boot mode, pulse width, expiration date, number of permissible uses, hours of permissible use, geographic region of permissible use, failure codes, and patient information.

75. The system of claim 72, further comprising a catheter interface device wherein the proximal end the catheter is operably connected to the catheter interface device and the operation console is operably connected to the catheter interface.

76. The system of claim 75, wherein the catheter interface device comprises a processor configured to transfer information from the operation console to the catheter.

* * * * *